(12) United States Patent
Weg

(10) Patent No.: US 7,776,831 B2
(45) Date of Patent: Aug. 17, 2010

(54) USE OF ANTIFUNGAL COMPOSITIONS TO TREAT UPPER GASTROINTESTINAL CONDITIONS

(76) Inventor: Stuart L. Weg, 498 Island Way, Franklin Lakes, NJ (US) 07417

( * ) Notice: Subject to any disclaimer, the term of this patent is extended or adjusted under 35 U.S.C. 154(b) by 290 days.

(21) Appl. No.: 11/668,764

(22) Filed: Jan. 30, 2007

(65) Prior Publication Data

US 2007/0196447 A1 Aug. 23, 2007

Related U.S. Application Data

(60) Provisional application No. 60/764,608, filed on Feb. 1, 2006, provisional application No. 60/833,433, filed on Jul. 26, 2006, provisional application No. 60/862,149, filed on Oct. 19, 2006.

(51) Int. Cl.
*A61K 31/70* (2006.01)
*A01N 43/04* (2006.01)
*C01B 31/34* (2006.01)
*C01B 21/22* (2006.01)
*C01B 21/24* (2006.01)

(52) U.S. Cl. .................... 514/31; 424/440; 424/400; 514/1

(58) Field of Classification Search .................... 514/31, 514/1; 424/440, 400
See application file for complete search history.

(56) References Cited

U.S. PATENT DOCUMENTS 4,238,475 A * 12/1980 Witzel et al. .................. 424/48
5,595,743 A * 1/1997 Wu .............................. 424/728
6,051,235 A * 4/2000 Theuer ........................ 424/756
6,217,886 B1 * 4/2001 Onyuksel et al. ............. 424/401
2004/0109894 A1 6/2004 Shefer et al.
2004/0209954 A1 10/2004 Lukacsko
2004/0254172 A1 12/2004 Landau et al.
2005/0074489 A1 4/2005 Gonzales et al.
2006/0024238 A1* 2/2006 Barth et al. ................... 424/45

FOREIGN PATENT DOCUMENTS

WO WO 01/39749 A2 6/2001

OTHER PUBLICATIONS

Merck_Nystatin (http://www.merck.com/mmpe/sec14/ch180/ch180b.html?qt=nystatin& alt=sh#sec14-ch180-ch180b-1538) p. 1-5.*
Dismukes et al. (CID,2000) p. 653-57.*
Stergiopoulou_2008 (Antimicrobial Agents and Chemotherapy, Jun. 2008), p. 2196-2104.*
Nystatin document -(http://www.webhealthcentre.com/drugix/Nystatin_DI0099.aspx) 2009.*
Upper GI Disorders document (http://faculty.ucc.edu/nursing-gervase /UGI%20Disorders.pps) -2009.*

* cited by examiner

*Primary Examiner*—Sreeni Padmanabhan
*Assistant Examiner*—Umamaheswari Ramachandran
(74) *Attorney, Agent, or Firm*—Klauber & Jackson LLC

(57) ABSTRACT

The present invention provides a novel method for treating oral conditions and upper gastrointestinal conditions in a subject by providing an inventive oral dosage form of a pharmaceutical composition comprising an effective amount of at least one antifungal and optionally a flavor modifier and/or salivation component such as an herbal component. In the present invention, the subjects have either not been diagnosed or do not have active or recurrent fungal infections. Specifically, the present invention is directed to chewable dosage forms.

11 Claims, No Drawings

USE OF ANTIFUNGAL COMPOSITIONS TO TREAT UPPER GASTROINTESTINAL CONDITIONS

CROSS-REFERENCE TO RELATED APPLICATIONS

This application claims priority under 35 U.S.C. §119, based on U.S. Provisional Application Ser. No. 60/764,608, filed Feb. 1, 2006; Ser. No. 60/833,433, filed Jul. 26, 2006; and Ser. No. 60/862,149, filed Oct. 19, 2006, the disclosures of which are incorporated herein by reference in their entirety.

FIELD OF THE INVENTION

The present invention relates to methods and compositions for treating various conditions in the upper gastrointestinal tract. Specifically, the invention is directed to the use of antifungal dosage forms for treating upper gastrointestinal disease such as heartburn, reflux, gastroesophogeal reflux disease (GERD), gastritis, dyspepsia, and nausea associated with morning sickness. The present invention is also directed to the use of antifungal dosage forms for the treatment of oral conditions, including halitosis, dental plaque, gingivitis, xeorstomia, and dry mouth.

BACKGROUND OF THE INVENTION

Upper gastrointestinal (GI) diseases affect millions of people annually, leading to recurrent and discomforting symptoms. Exemplary GI diseases include heartburn, reflux, gastroesophogeal reflux disease (GERD), gastritis, and dyspepsia.

Heartburn, or pyrosis, is a sensation of pain or burning located substernally or high in the epigastrium with radiation into the neck and occasionally to the arms. Heartburn is associated with the regurgitation of acid-peptic gastric juices into the esophagus. Acid reflux can lead to heartburn in milder cases and to gastroesophageal reflux disease in severe cases. Reflux symptoms are often treated as an acid problem, and a typical remedy is an antacid. GERD, also referred to as reflux or reflux esophagitis, is a clinical condition in which the reflux of stomach acid into the esophagus is frequent and severe enough to impact a patient's normal functioning, to cause discomfort or pain, and/or to cause damage to the esophagus. It has been estimated by the U.S. Department of Health and Human Services that about seven million people in the United States suffer from GERD.

Gastritis is pathologically an inflammatory process of the stomach, particularly of the gastric mucosa. It has been known that an acute gastritis is often induced by ingestion of anti-inflammatory agents (aspirin, etc.) or alcohol (ethanol), by emotional stress, or by the back-flow of bile into the stomach. Gastritis may occasionally result from a mistaken ingestion of corrosive acid or alkali.

Various approaches and medicines have been developed to treat upper GI conditions associated with damaged or malfunctioning mucosal tissues in the GI tract. Treatment of upper GI tract conditions has been carried out by the use of alkaline agents and gastric acid suppressors or by limiting consumption of foods to bland diets. One approach to relieve symptoms of reflux or gastritis has been to neutralize gastric acid by using antacids. For example, aluminum and magnesium hydroxide (MAALOX® and MYLANTA®) neutralize gastric acidity, resulting in an increase in stomach pH and duodenal bulb pH. Antacids are fast acting and temporary fixes of short duration. They are known to neutralize acid in the stomach and may also act locally in the distal esophagus. However, antacids do not always prevent heartburn when taken before food or beverages that may provoke symptoms.

Another approach to treat upper GI conditions has been to use $H_2$-receptor antagonists, also known as $H_2$-blockers, to inhibit the action of histamine on the parietal cell, which inhibits acid secretion. Examples of $H_2$-receptor antagonists include cimetidine (TAGAMET®), nizatidine (AXID®), ranitidine hydrochloride (ZANTAC®), lansoprazole (PREVACID®), rabeprazole (ACIPHEX®), and famotidine. U.S. Pat. No. 5,667,794 (to Simon et al.) discloses famotidine, an exemplary $H_2$-receptor antagonist used for the treatment of upper GI conditions. However, for many of these medications, there is a delay between consumption and relief from symptoms. Additionally, treatment can be quite costly to the average patient.

Alternatively, upper GI conditions have been treated with proton-pump inhibitors ("PPIs") which reduce the amount of gastric acid produced by gastric acid-producing cells. These prescription medications include lansoprazole (PREVACID®), esomeprazole (NEXIUM®), omeprazole (PRILOSEC®), pantoprazole (PROTONIX®), and omeprazole IR (ZEGERID®). However, similar to the $H_2$-blockers, the most popular PPIs require a prescription and demonstrate a delay between consumption and relief from symptoms. Various proton pump inhibitors and treatments of GI disorders are disclosed in U.S. Pat. No. 6,132,770 (to Lundberg); U.S. Pat. No. 6,869,615 (to Chen, et al.); and U.S. Pat. No. 4,786,505 (to Lovgren, et al.).

To solve some of the difficulties associated with current treatments, combination treatments of antacids with $H_2$-receptor antagonists or PPIs have been proposed. However, recent studies have shown that $H_2$-receptor antagonists or and PPIs may cause and increase incidence of hip fractures. (See Yang et al., JAMA. 2006 Dec. 27; 296(24):2947-53). U.S. Pat. No. 5,229,137 (to Wolfe) describes compositions and methods which require the simultaneous administration of an $H_2$-receptor antagonist with an antacid to provide immediate, lasting relief from pain, discomfort and symptoms associated with episodic heartburn. WO 92/00102 describes co-administration of $H_2$-receptor antagonists with antacids for treating gastric disorders such as hyperacidity. WO 93/12779 describes compositions of $H_2$ antagonists with antacids for treating gastric disorders such as hyperacidity. U.S. Pat. No. 5,817,340 describes compositions of famotidine with antacids for treating gastrointestinal distress.

U.S. Pat. No. 4,861,592 describes oral compositions containing cimetidine and aluminum hydroxide-magnesium carbonate co-dried gel for treating duodenal, gastric, recurrent and stomal ulceration, and reflux esophagitis. U.S. Pat. No. 4,824,664 describes effervescent compositions containing cimetidine and sodium bicarbonate for treating duodenal and gastric ulcers. U.S. Pat. Nos. 5,169,640 and 5,188,839 describe compositions containing cimetidine, aluminum hydroxide gel, and magnesium hydroxide, for treating duodenal, gastric, recurrent and stomal ulceration, and reflux esophagitis.

While the methods in art have some effectiveness in relieving the pain and discomfort associated with upper GI symptoms, there exists a need for developing innovative compositions and methods for preventing and treating upper-GI symptoms (related to acid reflux) that can be taken quickly, inexpensively, and with fast resolution of symptoms. The present invention addresses these needs with the novel use of antifungal agents.

SUMMARY OF THE INVENTION

The present invention provides a method for treating upper gastrointestinal conditions in a subject, which method includes administering to the subject in need thereof a solid oral dosage form of a pharmaceutical composition containing an effective amount of an antifungal and, wherein the subject has not been diagnosed with a gastric or esophageal fungal infection. In certain embodiments of the invention, the pharmaceutical composition further comprises a flavor modifier and/or one or more herbal component and/or a vitamin component. In particular embodiments, the oral dosage form comprises a component that induces salivation, including for example an herbal component.

In one embodiment, at least one antifungal is selected from the group consisting of nystatin, nystatin dehydrate, nystop, mycostatin, bio-statin, mykinac, nilstat, nystex, o-v statin, amphotericin, amphotericin B, amphotec, fungizone, undecyne, undecylenic acid, zinc undecylenate, gentian, amphocin, gentian root, gentian violet, and combinations thereof. In a preferred embodiment, the antifungal is nystatin.

In certain embodiments, the effective amount of nystatin ranges from about from about 10,000 units to about 1,000,000 units in powder form. More particularly, the amount ranges from about 50,000 units to about 500,000 units, even more particularly from about 80,000 to about 200,000 units. The oral dosage form is administered at least once a day.

In a specific embodiment, the oral dosage form is a solid oral controlled release form; in particular, it can be selected from a group consisting of a tablet, capsule, particle, powder, sachet, a wafer, a chewable tablet, a buccal tablet, a sublingual tablet, a quick-dissolve tablet, an effervescent tablet, a granule, a pellet, a bead, a pill, a troche, a sprinkle, a film, a dry syrup, a reconstitutable solid, a suspension, pastille, lozenge, gum, lollipop, chewing gum or chewable candies, pouch or plugs (similar to chew/dip strands), caplet, or a strip. In a specific embodiment, the oral dosage form is a pastille, lozenge, chewing gum, chewable candy, pouch or plug.

According to the invention, the upper gastrointestinal condition is selected from the group consisting of active benign gastric ulcer, gastroesophageal reflux disease (GERD), Zollinger-Ellison syndrome, erosive esophagitis, indigestion gastric reflux, dyspepsia, reflux disease, or nausea associated with morning sickness.

The present invention also provides for the treatment of oral conditions including halitosis, dental plaque, gingivitis, xerostomia, dry mouth, oral malodor and combinations thereof.

In one specific embodiment, the compositions are used in the evening or at night before sleep to aid in controlling or preventing snoring, night coughing, aspirations (and therefore aspirational pneumonia).

The invention also provides for the oral dosage form containing a pharmaceutical composition, which includes an effective amount of an antifungal; preferably a flavor modifier; and a carrier. In certain embodiments, the solid oral dosage form further contains at least one additive selected from the group consisting of: an excipient, a diluent, a disintegrant, a lubricant, a plasticizer, a colorant, a dosing vehicle, and any combination thereof.

The compositions of the present invention may also contain one or more additives selected from the group consisting of betaine hydrochloride, betaine beta carotene, vitamin E, selenium, vitamin B-6, folic acid, vitamin C, magnesium, vitamin B-1, vitamin B-2, niacinamide, vitamin B-12, zinc, copper, biotin, pantothenic acid, dandelion root, acidophilus dairy free, bifidus dairy free, FOS powder, chromium polynicotinate, betaine HCl, pancreatin, papain, and pepsin.

DETAILED DESCRIPTION

It has now been discovered that antifungal compounds, such as nystatin, can be effectively used to achieve the desired symptomatic relief of upper gastrointestinal conditions. The invention is based in part on the unexpected discovery that sustained release of nystatin is capable of resolving gastroesophageal reflux disease (GERD) in otherwise healthy adults.

The subject invention advantageously provides a dosage form for oral administration containing an antifungal medicament to treat symptoms of upper gastrointestinal conditions. The treatable symptoms include but are not limited to heartburn, indigestion, acid reflux, reflux esophagitis, gastroesophageal reflux disease, gastritis, dyspepsia and other acid-related upper GI conditions. In a further embodiment, treatable symptoms include nausea associated with pregnancy, e.g., morning sickness. It has been discovered that the oral dosage form is beneficial in the treatment of upper GI conditions in individuals not diagnosed with or does not have a gastric fungal infection. The antifungal oral dosage form provides sustained relief of discomforting symptoms and lasting therapeutic effect.

The terms used in this specification generally have their ordinary meanings in the art, within the context of this invention and in the specific context where each term is used. Certain terms are defined below to provide additional guidance in describing the compositions and methods of the invention and how to make and use them.

Definitions

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "prevent" or prevention is used in terms of prophylactic administration of a pharmaceutical composition prior to the onset of disease or to prevent recurrence of a disease. Administration of the oral dosage form to prevent the disease need not absolutely preclude the development of symptoms. Prevent can also mean to reduce the severity of the disease or its symptoms.

The phrase "pharmaceutically acceptable" as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "therapeutically effective" as applied to dose or amount refers to that quantity of a compound or pharmaceutical composition that is sufficient to result in a desired activity upon administration to a mammal in need thereof. As used herein with respect to the pharmaceutical compositions comprising an antifungal, the term "therapeutically effective amount/dose" refers to the amount/dose of a compound or pharmaceutical composition that is sufficient to produce an effective response upon administration to a mammal.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The term "amount" as used herein refers to quantity or to concentration as appropriate to the context. In the present invention, the effective amount of an antifungal compound refers to an amount sufficient to treat symptoms associated with upper gastrointestinal diseases. The effective amount of a flavor modifier refers to an amount sufficient to counter the bad tastes of antifungal compounds. The effective amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors.

"Nausea associated with pregnancy" refers to morning sickness, evening sickness, and hyperemesis gravidarum, without limitation.

Pharmaceutical Formulation

The pharmaceutical formulations of the present invention are directed to use of oral dosage forms comprising at least one antifungal active ingredient to treat upper GI conditions; in some cases, without testing for a fungal infection. In specific embodiments, the oral dosage form includes at least one flavor modifier, and additives as necessary including, for example, bases, stabilizers, and/or fillers.

As used herein, the term "active ingredient" or "active agent" refers to one or more compounds that have some antifungal property. Accordingly, more than one type of antifungal compound may be added to the formulation of the invention. The formulation of the invention may comprise any pharmaceutically acceptable antifungal that may be orally administered to a subject. Formulations including active ingredients in amounts appropriate for the desired pharmacological properties at the dosage administration can be prepared. An "active ingredient" of the present invention can be any non-active compound, including but not limited to antifungals, $H_2$-blockers, and proton pump inhibitors.

Antifungals

The pharmaceutical compositions of the present invention include at least one active ingredient that is a pharmaceutically acceptable antifungal agent. Exemplary antifungal agents include, but are not limited to, at least on of the following: nystatin, amphotericin B, natamycin, miconazole, ketoconazole, clotrimazole, econazole, mebendazole, bifonazole, butoconazole, fenticonazole, isoconazole, oxiconazole, sertaconazole, sulconazole, thiabendazole, tiaconazole, fluconazole, itraconazole, ravuconazole, posaconazole, voriconazole, terbinafine, amorolfine, naftifine, butenafine, caspofungin, micafungin, flucytosine, undycene, undecylenic acid, zinc undecylenate, gentian, griseofulvin, gentian root, gentian violet, and combinations thereof. Examples of imidazole antifungals are disclosed in U.S. Pat. No. 6,656,928 (to McAdden), which is incorporated herein by reference.

In a specific embodiment of the invention, the antifungal is nystatin. Nystatin is disclosed, for example, in U.S. Pat. No. 4,006,222 (to Metzger), which is incorporated herein by reference in its entirety. In another embodiment, the antifungal is amphoteracin B, as disclosed for example in U.S. Pat. No. 4,902,789 (to Michel, et al.), also incorporated herein by reference in its entirety.

The antifungal is present in each dosage form in amounts ranging from about 5,000 units to about 1,000,000 units in powder form. Preferably, the amount ranges from about 50,000 units to about 500,000 units, more preferably from about 80,000 to about 200,000 units.

In certain embodiments, the dosage form may include a combination therapy with one or more active ingredients, including but not limited to antacids or H-blockers. For example, an embodiment may contain an antifungal and a histamine $H_2$-receptor antagonist. Examples of $H_2$-receptor antagonists include cimetidine (TAGAMET®), nizatidine (AXID®), ranitidine hydrochloride (ZANTAC®), rabeprazole (ACIPHEX®), and famotidine. U.S. Pat. No. 5,667,794 (to Simon et al.), incorporated herein by reference, discloses famotidine, an exemplary $H_2$-receptor antagonist used for the treatment of upper GI conditions.

Alternatively, embodiments may contain an antifungal and a proton pump inhibitor. Examples of PPIs include but are not limited to lansoprazole (PREVACID®), esomeprazole (NEXIUM®), omeprazole (PRILOSEC®), pantoprazole (PROTONIX®), and omeprazole IR (ZEGERID®). Various proton pump inhibitors are disclosed in U.S. Pat. No. 6,132,770 (to Lundberg); U.S. Pat. No. 6,869,615 (to Chen, et al.); and U.S. Pat. No. 4,786,505 (to Lovgren, et al.), all of which are incorporated herein by reference in their entirety.

Flavor Modifiers

In certain embodiments, the pharmaceutical composition of the present invention also preferably includes at least one flavor modifier. The flavor modifiers, or taste masking components, are components to mask or lessen the unpleasant tastes commonly known to be associated with antifungal compounds. Inclusion of taste masking components is particularly desirable when administration is prolonged in the oral cavity, such as compositions in the form of lozenges. Non-limiting examples of taste masking components include fruit flavorings, mint flavorings, salt, or sweeteners.

Examples of sweeteners include, but are not limited to, stevia (stevioside), Nutrasweet, and Splenda, as well as any non-nutritive sweeteners, also called sugar substitutes or artificial sweeteners, including but not limited to saccharin, cyclamate, aspartame, sucralose, and acesulfame potassium. Additionally, sugar alcohols or other nutritive sweeteners derived from fruits or produced commercially from dextrose may be used. The most common include: sorbitol, mannitol, xylitol, maltitol, sorbitol, and mannitol. In some embodiments, the flavor modifiers do not contain sugar and the dosage form is sugar-free. In a specific embodiment, the sweetener is stevia.

U.S. Pat. No. 5,972,374 (to Theisen), U.S. Pat. No. 5,523,105 (to Ishikawa, et al.), and U.S. Pat. No. 5,425,962 (to Johnson, et al.) disclose mint oils and flavorants and their uses in various products such as gum and medications. Other exemplary flavor modifiers and/or flavorants include, but are not limited to fruit flavorings such as grape, cherry, lemon, or other citrus flavors; other acceptable nonfood flavorings such as tutti frutti flavor; and herbal flavorings. Flavor modifiers may be artificial or juice extracts.

The flavor modifiers may be present in varying amounts, depending on the particular antifungal used. In certain embodiments, the flavor modifiers are present in amounts ranging from about 5 mg to about 100 mg per dosage form, preferably from about 20 mg to about 50 mg per dosage form.

Herbal Components

The pharmaceutical composition of the present invention may also includes at least one component that induces salivation. In particular, the pharmaceutical composition includes an herbal component that induces salivation. Inducing salivation in a subject improves the efficacy of the composition and ultimately enhances treatment of the gastrointestinal conditions.

Any components which will promote salivation may be used in the present invention. In particular, bitter herbs are used to promote salivation. Herbal component(s) of the present invention can be selected from a group consisting of, but not limited to, ginger, senega root, gentian, motherwort, hops, dandelion, papaya, dock or sorrel, sunflower, calendula, nasturtium, mallow, chicory, corn silk, clover and mixtures thereof. In other embodiments, nonherbal salivation enhancing components are also contemplated.

The salivation inducing components may be present in varying amounts, depending on the particular antifungal used and depending on what particular dosage form is used.

Vitamins or Food Additives

The therapeutic composition of the present invention may also contain vitamins or food additives that deliver or increase hydrochloric acid, gastric juices, and enzymes. Such additives include but are not limited to an effective amount of betaine hydrochloride, betaine beta carotene, vitamin E, selenium, vitamin B-6, folic acid, vitamin C, magnesium, vitamin B-1, vitamin B-2, niacinamide, vitamin B-12, zinc, copper, biotin, pantothenic acid, dandelion root, acidophilus dairy free, bifidus dairy free, FOS powder, chromium polynicotinate, betaine HCl, pancreatin, papain, and pepsin.

Dandelion Root supports the digestive tract. It primarily works with the liver and gallbladder by stimulating digestive enzymes produced by each organ. It also stimulates digestion and can help with those who suffer from constipation and acid reflux. This herb is also high in many vitamins and minerals. Vitamins found in food are better absorbed and retained by the body. These types of additive ingredients not only giving the digestive system support, but also by giving a natural source of vitamins and minerals. Other additives such as kelp, sea vegetation, alfalfa, trace minerals, and molybdenum, which also have high concentrations of minerals, could be substituted. As for digestive support, other items such as juniper, aloe vera, burdock, ginger root, and artichoke also have potent effects on supporting the digestive tract and could be substituted.

Probiotic (acidophilus dairy free/bifidus dairy free) bacteria favorably alter the intestinal micro-flora balance, inhibit the growth of harmful bacteria, promote good digestion, boost immune function, and increase resistance to infection. Individuals with flourishing intestinal colonies of beneficial bacteria are better equipped to fight the growth of disease-causing bacteria. Probiotics are important in finishing the digestive process and therefore can increase the absorption of nutrients.

Fructo-oligosaccharides (FOS) are naturally occurring carbohydrates that cannot be digested or absorbed by humans but support the growth of bifidobacteria, one of the beneficial bacterial strains. Friendly bacteria support digestion, elimination and the absorption of nutrients in the body.

Betaine (hcl/gastric acid) may also be added to the compositions of the present invention. One of the most important parts of digestion occurs in the stomach, where gastric (stomach) acid helps break down proteins for further digestion in the small intestine. This increased digestion aids in the absorption of nutrients that support the nervous system.

Papain/Pancreatin/Pepsin are digestive enzymes (also called pancreatic enzymes) include three classes of enzymes: proteolytic enzymes needed to digest protein, lipases needed to digest fat, and amylases needed to digest carbohydrates. Pancreatic enzymes should be used with to support the digestive process. Allergies are triggered by partially undigested protein, while protoolytic enzymes reduce allergy symptoms. Proteolytic enzymes such as trypsin, chymotrypsin, and bromelain are partially absorbed by the body. Proteolytic enzymes may improve immune system function, a common problem with people with allergies and nervous system weakness. Papain, pancreatin and, pepsin are contemplated in the compositions of the present invention, however other items such as papaya, and pineapple also have high concentrations of these digestive enzymes could be substituted.

Any suitable medicament for oral cleansing, breath freshening or the like can be added to the film formulation. The medicaments can include, for example, a pH control agent, such as urea and buffers, inorganic components for tartar or caries control, such as phosphates and fluorides, a breath freshening agent, such as zinc gluconate, an anti-plaque/anti-gingivitis agent, such as chlorohexidene, CPC, and triclosan, a saliva stimulating agent including, for example, food acids such as citric, lactic, maleic, succinic, ascorbic, adipic, fumaric and tartaric acids, a pharmaceutical agent, a nutraceutical agent, a vitamin, a mineral, other like medicaments or combinations thereof.

Additional Additives

The therapeutic composition of the present invention may also contain additional additives, including polymer or therapeutic agent stabilizers, such as but not limited to sucrose, salts, and pH adjusting agents; and preservatives including antioxidants such as butylated hydroxytoluene, and antibacterials. Alternative additives are disclosed in detail below.

Thus, the pharmaceutical composition may include one or more additives, depending on the pharmaceutically acceptable carrier, a base, a preservative, a dye, a binder, a suspending agent, a dispersing agent, a stabilizer, a colorant, a disintegrant, an excipient, a diluent, a lubricant, a plasticizer, an oil or any combination of any of the foregoing. Suitable pharmaceutically acceptable additives include, but are not limited to, ethanol; water; glycerol; aloe vera gel; allantoin; glycerin; vitamin A and E oils, citric acid; mineral oil; PPG2 myristyl propionate; vegetable oils and solketal. Examples of additional additives include, but are not limited to, sorbitol; talc; stearic acid; and dicalcium phosphate.

Suitable binders, fillers and/or bases include, but are not limited to, starch; gelatin; natural sugars, such as glucose, sucrose and lactose; corn sweeteners; natural and synthetic gums, such as acacia, tragacanth, vegetable gum, and sodium alginate; carboxymethylcellulose; polyethylene glycol; waxes; and the like.

Suitable disintegrators include, but are not limited to, starch such as corn starch, methyl cellulose, agar, bentonite, xanthan gum and the like.

Suitable lubricants include, but are not limited to, sodium oleate, sodium stearate, magnesium stearate, sodium acetate, and the like.

The composition may also include suitable preservatives, e.g., sodium benzoate, and other additives the may render the composition more suitable for application, e.g., sodium chloride, which affects the osmolarity of the preparation.

Suitable dispersing and suspending agents include, but are not limited to, synthetic and natural gums, such as bentoite, vegetable gum, tragacanth, acacia, alginate, dextran, sodium carboxymethylcellulose, methylcellulose, polyvinyl-pyrrolidone and gelatin.

A suitable pharmaceutical diluent is, but is not limited to, water.

Under ordinary conditions of storage and use, the preparations of the present invention can also contain a preservative to prevent the growth of microorganisms. The therapeutic composition can be stable under the conditions of manufacture and storage and preferably preserved against the contaminating action of microorganisms such as bacteria and fungi. A carrier liquid can be a solvent of dispersion medium containing, for example, water, ethanol, polyol (e.g., glycerol, propylene glycol, and liquid polyethylene glycol, and the like), and suitable mixtures thereof. The prevention of the action of microorganisms can be brought about by various antibacterial and antifungal agents, for example, parabens, chlorobutanol, phenol, sorbic acid, thimerosal, benzoic acid, alcohol, benzalkonium chloride and the like. In many cases, it will be preferable to include isotonic agents, e.g., sugars, phosphate buffers, sodium benzoate, sodium chloride, or mixtures thereof.

Modes of Administration

The therapeutic composition can be administered in a variety of oral dosage forms adapted to the chosen route of administration. Administration in this situation can include, for example, use of a tablet, capsule, particle, powder, sachet, pastille (e.g., as disclosed in U.S. Pat. No. 4,725,440), lozenge, chewing gum, chewable candies (i.e. gummy type or taffy) pouch or plugs (similar to chew/dip strands), lollipop, caplet, coated or encapsulated chewable capsules, or other solid oral dosage form of the formulation. In particular, the solid oral dosage form is a chewing gum or chewable candy, which while being sustained in the mouth, the nystatin is slowly dissolved and mixed with saliva. The saliva is then swallowed thereby coating mucosal surfaces in the esophagus, esophagogastric (EG) junction, and stomach, particularly the antrum of the stomach.

In a specific embodiment, the solid oral dosage form may be in the form of an edible wax. The dosage form is made according to known methods in the art, including for example, heating an edible wax at a temperature above its melting point; heating an edible oil at a temperature above the melting point of the edible wax; mixing the melted wax with the oil along with the pharmaceutical formulation, and homogenizing the mixture.

In yet another embodiment, the antifungal agent can be formulated for sublingual and/or oral pharyngeal administration. For example, nystatin can be incorporated in a chewable "candy" matrix, such as that described in U.S. Pat. No. 4,671,953 (to Stanley, et al.), or in a gum base.

The oral dosage forms of the present invention provide the advantage of a sustained-release system, whereby effective amounts of antifungal are released over time. Various types of sustained-release materials have been established and are well known by those skilled in the art.

Methods of Treatment

The therapeutic composition of the present invention may be administered to a host subject (patient) to achieve any desired effect in the clinical outcome of the targeted upper gastrointestinal condition. Preferably the subject is a mammal, and more preferably a human. The human may be from an adult or pediatric population.

Specifically, in the present invention, the subject is one who has either not been diagnosed with a fungal infection or who has not been diagnosed with recurrent fungal infections. The present invention is directed to subjects needing relief and treatment of upper gastrointestinal diseases, independent of any fungal infection (i.e., candida).

The terms "upper gastrointestinal condition" refers to symptoms affecting the proximal part of the gastrointestinal tract, which consists of the mouth, pharynx, esophagus, and stomach (including the antrum, pylorus and pyloric sphincter proximal to the pylorus valve).

The compositions of the invention may be used for the treatment or prevention of gastrointestinal conditions. Such conditions include, but are not limited to: gastritis; peptic ulcer; reflux esophagitis; dyspepsia; gastric ulcers; gastroesophageal reflux disease (GERD); severe erosive esophagitis; and pathological hypersecretory conditions such as Zollinger Ellison Syndrome. The methods and composition of the present invention may also be useful in the treatment of *H. pylori* infection and conditions associated with *H. pylori* infection (e.g., ulcers, gastric carcinoma, non-ulcer dyspepsia, gastritis, and esophageal lesions associated with gastroesophageal reflux disease). Other examples of the gastrointestinal disorder include, but are not limited to, gastrointestinal diseases, such as acute gastritis, chronic superficial gastritis, atrophic gastritis, antral gastritis, senile gastritis, bile-regurgitational gastritis, esophagitis, gastric neurosis, as well as various consequent conditions including gastric hyperacidity, hypochlorhydria, gastrointestinal discomfort after meals, gastritis caused by taking acidic drugs such as salicylates (e.g., aspirin), gastric discomfort after drinking, and gastric discomfort due to fasting. Symptoms often associated with these conditions include indigestion, heartburn, burping, coughing, wheezing, chest pain, stomach pain, feeling bloated, emesis, and hematemesis. U.S. Pat. Nos. 5,601,848 and 5,256,684 (to Marshall), and U.S. Pat. No. 5,977,159 (to Fandriks, et al.) disclose treatment of a variety of these upper GI disorders, and are incorporated herein by reference in their entirety. The present invention also provides the benefit of reducing or eliminating the use of $H_2$-receptor antagonists or PPIs, thereby reducing the incidence of hip fractures.

In another embodiment of the present invention, the pharmaceutical compositions are used to treat morning sickness in pregnant women. In particular embodiments, the classic nausea and vomiting in early pregnancy is treated. Cases can range in degree from mild to severe, and symptoms usually begin soon after the first missed period. Morning sickness, i.e., nausea and vomiting experienced during the first and second trimesters of pregnancy, is experienced by approximately half of all pregnant women, however it is particularly common in cases of multiple pregnancy and hydatidiform mole. (Kousen, M., "Treatment of nausea and vomiting in pregnancy", Am Fam Physician, 48:1279 (1993)). These symptoms appear to be related to hormonal issues in early pregnancy. These women may or may not have heartburn or signs of GERD and are previously not symptomatic people who have a self limiting disease. In another embodiment, the pregnant women may have preexisting disease (although may not be symptomatic) such as GERD or dyspepsia who develop those GI symptoms during the pregnancy that appear related to the preexisting condition with exacerbation due to anatomical changes or other pregnancy issues. This development may occur at any time during pregnancy. Hyperemesis gravidarum, i.e., persistent nausea and vomiting during pregnancy, can lead to a reduction in fluid and electrolyte levels, as well as a jeopardized nutritional status if the condition is not treated. The condition is characterized by prolonged and severe nausea and vomiting, dehydration, ketosis, and body weight loss. Other complications may include hyponatraemia, hypokalaemia, a low serum level, metabolic hypochloraemic alkalosis, ketonuria, liver function test abnormalities, abnormal thyroid function tests, and suppressed thyroid-stimulating hormone levels. Nelson-Piercy, C., "Treatment of nausea and vomiting in pregnancy. When should it be treated and what can be safely taken?", *Drug Saf,* 19(2):155-64 (1998).

In another embodiment of the present invention, the pharmaceutical compositions of the present invention may be used to treat oral conditions. The oral conditions include but are not limited to halitosis, dental plaque, gingivitis, xerostomia, dry mouth, oral malodor or combinations thereof. Halitosis is produced by the production and liberation of volatile compounds, mainly volatile derivatives of sulphur, such as hydrogen sulphide and methyl-mercaptane. According to the localization of the origin of the unpleasant odour, it can be classified as oral (localised in lips, tongue, teeth, dental prosthetic elements, periodontal tissues, oropharynx) or non-oral [caused by diseases of the respiratory tract, systemic diseases (hepatic dysfunction, cirrhosis, diabetic ketoacidosis, carcinomas and certain metabolic diseases in which an enzymatic anomaly occurs), diseases of the gastrointestinal tract and certain foods, drinks, tobacco and medicaments].

Treatment of these conditions is accomplished by administering to a patient an effective amount of the pharmaceutical composition according to the present invention. The effective amount may be administered once or multiple times daily, as necessary. Alternatively, the dosage form may be taken once every other day, or once or twice weekly.

Treatment duration can be short-term, e.g., several hours (for example 8-14 hours), or long-term, e.g., a number of days or indefinitely until the attending physician deems further administration no longer is necessary.

EXAMPLES

The present invention will be better understood by reference to the following proposed clinical study example, which is provided as exemplary of the invention, and not by way of limitation.

Example 1

Use of Nystatin Chewing Gum to Treat Indigestion

The present Example demonstrates the use of Nystatin chewing gum to treat indigestion. Once patients present with symptoms of indigestion, Nystatin chewing gum is prescribed to the patient. The Nystatin chewing gum is prepared with 100,000 units of nystatin (powder) and 30 mg stevia in a polyethene glycol base with tutti fruitti flavoring and citric acid as a stabilizer.

The patient is instructed to chew one piece of gum at the onset of indigestion symptoms. The chewing gum is sustained in the patient's mouth for at least 30 minutes, and repeated every 4 to 6 hours, or as needed. The chewing gum is taken for 10 consecutive days, and continued longer if necessary.

The symptoms of indigestion are reviewed at baseline, and at 1, 3, 5, 7 and 10 days following initiation of treatment.

Example 2

Use of Nystatin Lozenges to Treat Upper Gastrointestinal Conditions

The present Example provides a clinical trial protocol focusing on GERD, dyspepsia and heartburn, with dosages as low as 100,000 units of nystatin in sugar-free lozenges every other day.

Therefore, patients with these gastrointestinal conditions are a selected and treated with lozenges over a fixed time. Symptoms and other medication usage are measured before and after this therapy and then followed up to determine if there is improvement in treated patients symptoms and/or reduction in there medication use.

Patient Selection

Patient who have complaints of GERD, Heartburn or Dyspepsia and are under the care of a physician are acceptable for this trial with the following exceptions:
1) Under 14 years of age;
2) Pregnant or lactating;
3) New prescription medication of any type in the week before starting the trial;
4) New non-prescription or nutraseutical remedy for the above complaints within a week of this trial; and
5) Medically or surgically unstable (for example: new onset angina, treatment for *H. pylori,* uncontrolled hypertension or arrhythmia, Gaul bladder attack, etc.).

Treatment Protocol

One Lozenge (100,000 nystatin units/dose) is dissolved in the mouth three times a day. Lozenges are not taken within 30 minutes of eating and are not followed by any liquids for at least 20 minutes.

Patients are provided with a ten day supply of lozenges. They continue the trial medication until the supply is used or they cannot tolerate them.

Concurrent medications used for the above complaint such as prilosec, tums, etc. are permitted. Patients are encouraged to wean off these medications on their own as the trial progresses.

Documentation and Records

Pretrial: Brief medical history and vital signs including dosages of all medications and remedies listed. The patient's doctor must approve the patient for the study and "order" the medication.

Beginning point evaluation: "Please tell me how bad your daily complaint is." "On a scale of zero to ten, where zero is no symptoms at all and ten is your worst day ever." "How are you doing now with whatever remedy you may use?"

Post trial (immediately after finishing the course of lozenges): The patients are interviewed to determine what level the complaint is now at by repeating the zero to ten scale description used in the pretrial evaluation. Next, the interviewer must determine if any remedies used pretrial have been increased, decreased, changed, or stopped.

There should also be noted any other side effects, either positive or negative. The ordering doctor should be aware of all outcome information.

The patients should be seen again in at least a month to monitor if any improvement has been sustained.

Drop outs: Any patient who does not complete the trial should be questioned for adverse reactions, which should be reported to the doctor. The reason for dropping out should be noted. Data from a patient who starts a new medication or becomes medically or surgically unstable during the trial cannot be included in the results.

Summary and Discussion

Study Patients fall into three categories:
1) Symptomatic taking nothing
2) Symptomatic on a remedy
   a. Prescription
   b. non-prescription/nutraseutic
3) Not Symptomatic on a and/or b
End Points:
1) Improvement in the reported number scale of the patient; and/or
2) reduction or elimination of pretrial remedies.

Example 3

Use of Nystatin Lozenges to Treat Nausea Associated with Morning Sickness in Pregnant Women The present Example provides a clinical trial protocol focusing on the treatment of nausea associated with morning sickness in pregnant women, with dosages as low as 5,000 units of nystatin in sugar-free lozenges every day.

Patient Selection

Patients for this study experience nausea due to sickness during pregnancy. Patients can be at any stage of pregnancy. Patients may also experience GERD or dyspepsia.

Treatment Protocol

One lozenge (5,000 nystatin units/dose) is dissolved in the mouth three times a day. Lozenges are not taken within 30 minutes of eating and are not followed by any liquids for at least 20 minutes.

Patients are provided with a 14-day supply of lozenges. They continue the trial medication until the supply is used or they cannot tolerate them.

Concurrent medications used for nausea are permitted. Patients are encouraged to wean off these medications on their own as the trial progresses.

Documentation and Records

Pretrial: Brief medical history and vital signs including dosages of all medications and remedies listed. The patient's doctor must approve the patient for the study and "order" the medication.

Beginning point evaluation: "Please tell me how bad your daily complaint is." "On a scale of zero to ten, where zero is no symptoms at all and ten is your worst day ever." "How are you doing now with whatever remedy you may use?"

Post trial (immediately after finishing the course of lozenges): The patients are interviewed to determine what level the complaint is now at by repeating the zero to ten scale description used in the pretrial evaluation. Next, the interviewer must determine if any remedies used pretrial have been increased, decreased, changed, or stopped.

There should also be noted any other side effects, either positive or negative. The ordering doctor should be aware of all outcome information.

The patients should be seen again in at least a month to monitor if any improvement has been sustained.

Drop outs: Any patient who does not complete the trial should be questioned for adverse reactions, which should be reported to the doctor. The reason for dropping out should be noted. Data from a patient who starts a new medication or becomes medically or surgically unstable during the trial cannot be included in the results.

Summary and Discussion

Study Patients we capture fall into three categories:
1) Symptomatic taking nothing
2) Symptomatic on a remedy
   a. Prescription
   b. non-prescription/nutraseutic
3) Not Symptomatic on a and/or b
End Points:
1) Improvement in the reported number scale of the patient; and/or
2) reduction or elimination of pretrial remedies.

Example 4

Use of Nystatin Chewing Gum to Halitosis

The present Example demonstrates the use of Nystatin chewing gum to treat halitosis. Once patients present with symptoms of chronic or persistent halitosis (e.g., accompanying chronic sinusitis), Nystatin chewing gum is prescribed to the patient. The Nystatin chewing gum is prepared with 100,000 units of nystatin (powder) and 30 mg stevia in a polyethene glycol base with tuffi fruitti flavoring and citric acid as a stabilizer.

The patient is instructed to chew one piece of gum at the onset of indigestion symptoms. The chewing gum is sustained in the patient's mouth for at least 30 minutes, and repeated every 4 to 6 hours, or as needed. The chewing gum is taken for 10 consecutive days, and continued longer if necessary.

The symptoms of indigestion are reviewed at baseline, and at 1, 3, 5, 7 and 10 days following initiation of treatment.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for treating GERD in a subject, which comprises administering to the subject in need thereof a solid oral dosage form of a pharmaceutical composition consisting essentially of an effective amount of at least one antifungal, wherein the antifungal is selected from the group consisting of nystatin and nystatin dehydrate, and a flavor modifier.

2. The method of claim 1, wherein the subject has not been found to have a fungal infection.

3. The method of claim 1, wherein the antifungal is nystatin.

4. The method of claim 3, wherein the effective dosage amount of nystatin ranges from about 5,000 units to about 1,000,000 units per day.

5. The method of claim 4, wherein the effective dosage amount of nystatin ranges from about 50,000 units to about 500,000 units per day.

6. The method of claim 5, wherein the effective dosage amount of nystatin ranges from about 80,000 units to about 200,000 units per day.

7. The method of claim 1, wherein the flavor modifier is selected from the group consisting of fruit flavorings, mint flavorings, salt, and sweeteners.

8. The method of claim 7, wherein the flavor modifier is present in amounts ranging from about 5 mg to about 100 mg.

9. The method of claim 8, wherein the flavor modifier is present in amounts ranging from about 20 mg to about 50 mg.

10. The method of claim 1, wherein said oral dosage form is selected from the group consisting of a pastille, lozenge, chewing gum, chewable candy, pouch, and plugs.

11. The method of claim 1, wherein the solid oral dosage form is administered for at least one day.

* * * * *